United States Patent [19]

Glover et al.

[11] Patent Number: 4,659,677
[45] Date of Patent: Apr. 21, 1987

[54] METHOD PROVIDING LIQUID MIXING OUTSIDE CONTAINERS

[75] Inventors: Clyde P. Glover, Pittsford; Vratislav M. Michal, Rochester, both of N.Y.

[73] Assignee: Eastman Kodak Company, Rochester, N.Y.

[21] Appl. No.: 714,356

[22] Filed: Mar. 22, 1985

Related U.S. Application Data

[62] Division of Ser. No. 498,448, May 26, 1983, abandoned.

[51] Int. Cl.$^4$ .......................... G01N 1/00; B01L 3/02
[52] U.S. Cl. .................. 436/174; 73/863.32; 73/864.12; 73/864.13; 222/1; 222/137; 366/177; 366/348; 422/99; 422/100; 436/180; 604/56; 604/251
[58] Field of Search ............. 436/174, 179, 180; 422/68, 99, 100; 604/56, 80, 82, 83, 251, 252; 222/1, 137, 164, 165, 420; 73/863.32, 864.11, 864.12, 864.13, 864.14; 366/150, 177, 348

[56] References Cited

U.S. PATENT DOCUMENTS 2,661,870 12/1953 Huenergardt .
3,547,316 12/1970 Heiskell .
3,581,575 6/1971 Butler ......................... 73/864.12
3,976,429 8/1976 Ginsberg ................... 73/864.12 X
4,041,995 8/1977 Columbus .................. 422/100 X
4,135,561 1/1979 Senelonge .
4,141,833 2/1979 Cummins .
4,158,035 6/1979 Haase et al. .
4,181,700 1/1980 Chewenka et al. ............ 422/100 X
4,215,092 7/1980 Suovaniemi et al. ........... 73/863.32
4,341,310 7/1982 Sangiovanni et al. .
4,343,766 8/1982 Sisti et al. ................... 422/100 X
4,347,875 9/1982 Columbus .................... 222/108 X
4,441,532 4/1984 Hrubesh ...................... 422/99 X

FOREIGN PATENT DOCUMENTS 3008347 10/1980 Fed. Rep. of Germany ...... 422/100
7103370 9/1971 Norway .

Primary Examiner—Arnold Turk
Assistant Examiner—Robert J. Hill, Jr.
Attorney, Agent, or Firm—Dana M. Schmidt

[57] ABSTRACT

A device and method are described for forming a drop of two liquids pendent each from a separate platform. Means are included for moving the platforms from a spaced-apart position to one in which the drops contact each other and coalesce, while still pendent from the platforms.

6 Claims, 13 Drawing Figures

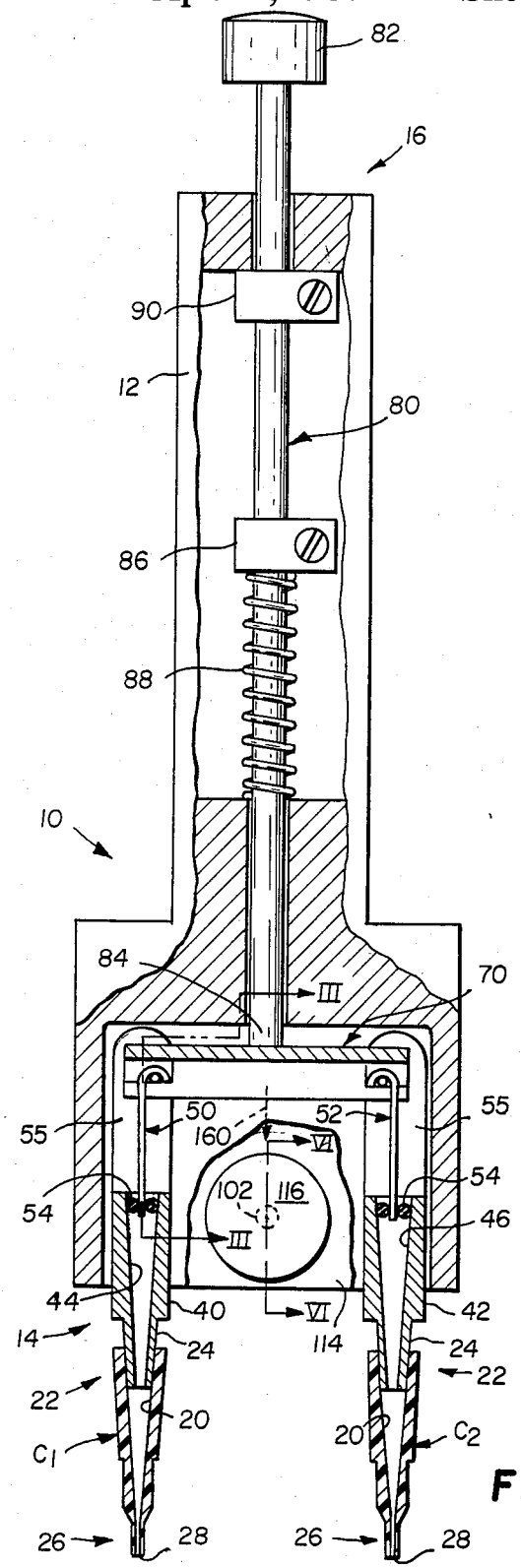
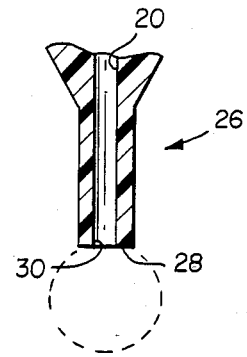
FIG. 2
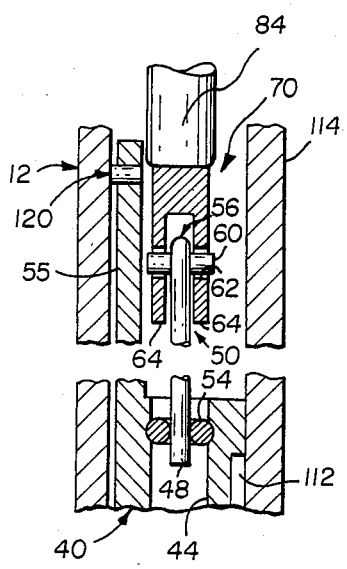
FIG. 3
FIG. 1

METHOD PROVIDING LIQUID MIXING OUTSIDE CONTAINERS

This is a division of application Ser. No. 498,448, filed May 26, 1983 now abandoned.

FIELD OF THE INVENTION

This invention relates to the metering of small quantities of mixed, low relative viscosity liquids.

BACKGROUND OF THE INVENTION

There is a need for a device that will allow intermixing of two small quantities (from about 5 to about 10 $\mu$l each) of low relative viscosity liquids, prior to the mixture being metered or dispensed onto or into some other element. An example of such a need is in the field of the immunoassay of biological analytes.

More specifically, recent advances in the analysis of biological liquids such as serum have allowed the use of as little as 10 $\mu$l of the liquid, for the test. Examples of test elements suitable for radiometric assays using such small amounts are described in U.S. Pat. Nos. 3,992,158, issued on Nov. 16, 1976, and 4,258,001, issued on Mar. 24, 1981. A large number of analytes have been proven to be amenable to such tests.

One portion of clinical analysis which would benefit from the use of such test elements is the field of immunoassay. Immunoassays usually involve the formation of an antibody-antigen complex in which known amounts of labeled antigen (or antibody) compete with unlabeled, unknown amounts of the same antigen (or antibody) from the patient. In conducting such tests, one procedure adds the labeled antigen or antibody as a diluent to the patient's sample immediately prior to adding the sample to the test element. The total liquid as diluted still preferably is only from about 10 $\mu$l to about 20 $\mu$l, to minimize the amount of labeled antigen or antibody that is required. Because of the porosity and high rates of flow present in test elements of the types described in the aforesaid U.S. patents, it is difficult in all embodiments to achieve such dilution or mixing by applying first a drop of the sample to such a test element, and then a drop of the diluent. The rapid absorption by the test element in such embodiments prevents the two sequentially added drops from mixing.

However, if the mixing of the diluent and patient sample occur within a container prior to contact with the test element, one or two problems are likely to occur: either the liquids will not intermix well because their small quantities will be spread out onto the walls of the container, or if intermixed, they still will be primarily on the container walls, with very little left to meter. The problem is particularly acute when, as in immunoassays, the diluent and the patient sample occupy about equal volumes, e.g., from about 5 $\mu$l of about 10 $\mu$l each.

Although conventional metering devices of various kinds have been available prior to this invention, none of them have been adequate to solve the aforementioned problems. For example, very complex devices have been constructed to cause a stream of drops to impinge on each other in mid-air. Such a system is generally unacceptable for clinical analysis metering, due to its complexity and instability.

SUMMARY OF THE INVENTION

As a solution to the afore-described problems, this invention provides a device and a method for mixing two low relative viscosity liquids outside of a container. The manner in which this is achieved is particularly useful to subsequent use of the coalesced and mixed drops in a clinical assay.

More specifically, in accord with one aspect of the invention there is provided a device comprising first and second dispensing chambers each constructed to dispense a low relative viscosity liquid therefrom, such as biological liquids. The device is improved in that it includes means for mixing the liquids outside the chambers, the mixing means comprising means for pressurizing the dispensing chambers, and moving means for providing relative movement of the dispensing chambers from a first position in which the chambers are spaced apart, to a second position in which the chambers are sufficiently proximate as to cause liquid dispensed from one chamber to coalesce and intermix with liquid dispensed from the other chamber, and thence to the first position.

In accord with the method aspect of the invention, a method of mixing two low relative viscosity liquids outside a container is provided. The method comprises the steps of (a) forming a drop of each of the liquids so as to be pendent from a platform, and (b) before, during or after step (a), moving the platforms from a first spaced-apart position to a second position in which the formed drops coalesce while still pendent from the platforms, and intermix.

Thus, it is an advantage of the device and method of the present invention that very small quantities of liquid can be intermixed in a form that permits substantially all of the intermixed liquid to be subsequently dispensed onto a test element.

It is a related advantage of this device and method that small amounts of diluent containing a labeled antigen or antibody can be admixed with a patient's serum sample prior to the mixture being dispensed onto an immunoassay test element.

It is a further advantage of this device and method that such mixing can be achieved without interfering with the aspirating function that obtains the liquids in the first place.

Other features and advantages will become apparent upon reference to the following Description of the Preferred Embodiment, when read in light of the attached drawings.

BRIEF DESCRIPTION OF THE DRAWINGS

FIG. 1 is an elevational view, partially broken away and sectioned along the midplane of a device constructed in accordance with the invention;

FIG. 2 is an enlarged, fragmentary and sectioned view of the dispensing end of the disposable container used with the device;

FIG. 3 is a fragmentary sectional view taken generally along the line III—III of FIG. 1, but with the moving means omitted for clarity;

DESCRIPTION OF THE PREFERRED EMBODIMENTS

Figure 4:
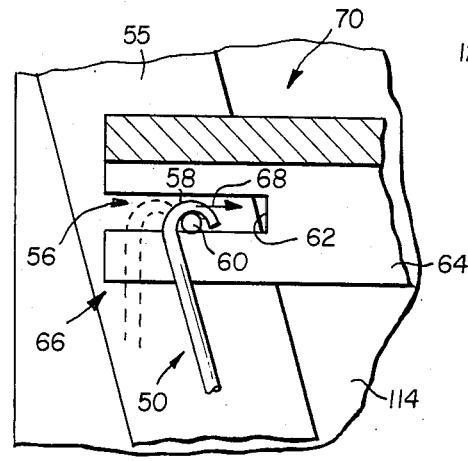
FIG. 4 is an enlarged, fragmentary elevational view similar to that of FIG. 1, showing the parts moved to a second, dispensing and mixing position.

We have discovered means by which small amounts of low relative viscosity liquids can be mixed outside a container, while maintained in a generally stable format.

The invention is hereinafter described as a hand-held pipette that is particularly useful in dispensing biological liquid for an immunoassay, the preferred embodiment, using disposable containers. In addition, the invention is useful as a device for providing mixing of low relative viscosity liquids outside of a container for any end use whatsoever, whether or not the device is a pipette. For example, low relative viscosity industrial liquids can be admixed by this invention. Furthermore, although the invention is particularly useful in admixing very small quantities, it is applicable to larger quantities as well. Still further, although the preferred embodiment is hand-held, the invention is also applicable to a metering device that is completely automated. Still further, the invention is applicable to such a device whether the dispensing chambers for the liquid are integral with the device, or are disposable containers.

As used herein, "biological liquids" means all liquids obtained from animals, including whole blood, serum, sweat, spinal fluid and urine, and low relative viscosity liquids compatible with these animal liquids, such as saline solutions and immunoassay diluents containing labeled antigens or antibodies. "Low relative viscosity", as used herein, means relative viscosities no greater than about 20 when compared against water measured at 25° C. Liquids having relative viscosities larger than this do not intermix well, over a reasonable time period, e.g., a few seconds, merely by coalescing with a drop of liquid having a different surface tension. For example, epoxies with a relative viscosity of 100 do not mix well enough by this mechanism, within a reasonable length of time, to allow their usage with this invention.

As shown in FIG. 1, a pipette 10 constructed in accordance with the invention comprises a generally hollow frame 12 having a front or dispensing end 14 and a rear or actuating end 16. To aspirate biological liquids into, and force a pendent drop to form on, two disposable containers $C_1$ and $C_2$, piston chambers 40, 42 and piston rods 50, 52 at end 14 are actuated by a connecting cross-member 70 operated by a plunger 80 and button 82 at end 16.

Considering first the dispensing end 14, pipette 10 is intended to be used with disposable containers $C_1$ and $C_2$, constructed as described, for example, in U.S. Pat. No. 4,347,875, issued on Sept. 7, 1982. That is, these containers have an internal bore 20 sloped to allow end 22 thereof to be force-fitted onto a tapered nipple 14 of piston chambers 40 and 42. The opposite ends 26 of containers $C_1$ and $C_2$ have a tapered structure adapted to prevent liquid that remains on the exterior after aspiration, from flowing down to an interfering position adjacent to platform 28 of the container. Platform 28, FIG. 2, is especially constructed as described in U.S. Pat. No. 4,041,995, to allow liquid expressed from aperture 30 surrounded by and centered generally within platform 28, to remain pendent from the platform as shown by the dotted meniscus shape. The details of the '995 patent concerning the platform configuration are expressly incorporated herein by reference.

Piston chambers 40 and 42 have an internal diameter 44 and 46, FIGS. 1 and 3, constructed to accommodate ends 48 of piston rods 50 and 52, as is conventional. Seals such as O-rings or quad seals 54 allow the insertion and withdrawal of rods 50 and 52 to generate pressure or an aspirating vacuum, respectively, within the chambers and thus on liquid in or outside of, respectively, containers $C_1$ and $C_2$. Each entire piston chamber 40 and 42 is mounted within frame 12 by a flange 55 that is secured as described hereinafter.

Ends 56 of piston rods 50 and 52 are secured to cross-member 70 so that both rods are simultaneously moved when cross-member 70 is moved. More specifically, FIGS. 3 and 4, ends 56 are hooked at 58 to accommodate within the hook a pin 60. Pin 60 in turn extends the thickness of member 70, through slots 62. Cross-member 70 preferably is a U-shaped channel having flanges 64, the end portions 66 of which bear slots 62, FIG. 4. The depth of slots 62 is such that pin 60 is free to slide into cross-member 70, as indicated by arrow 68, FIG. 4, when cross-member 70 is depressed and containers $C_1$ and $C_2$ are moved together, as described hereinafter.

Cross-member 70 is joined to plunger 80 at end 84 of the plunger, FIG. 1. A locking flange 86 is secured around plunger 80 intermediate button 82 and end 84. A compression return spring 88 is mounted between flange 86 and a portion of frame 12. To control the amount of return travel of plunger 80 and of the withdrawal of rods 50 and 52 from chambers 40 and 42, a locking flange 90 is adjustably secured around plunger 80 within frame 12 at end 16 thereof.

In accordance with one aspect of the invention, to move containers $C_1$ and $C_2$ from their spaced-apart position shown in FIG. 1, to one in which the containers are so close as to cause their pendent drops to contact each other, moving means are provided. Such means comprise, FIGS. 5 and 6, a rotatable disc 100 mounted on or integral with a rotatable pin 102 journalled to frame 12. Links 104 and 106 are pivotally connected at their ends 108 to disc 100, off-center from pin 102. The opposite ends 110 of links 104 and 106 are respectively journalled to a portion of chambers 40 and 42 that is preferably recessed at 112, FIG. 5, to receive the links. Pin 102 extends outward beyond frame 12 at one surface 114, FIGS. 1 and 6, to accommodate a control knob 116 secured thereto.

Figure 5:
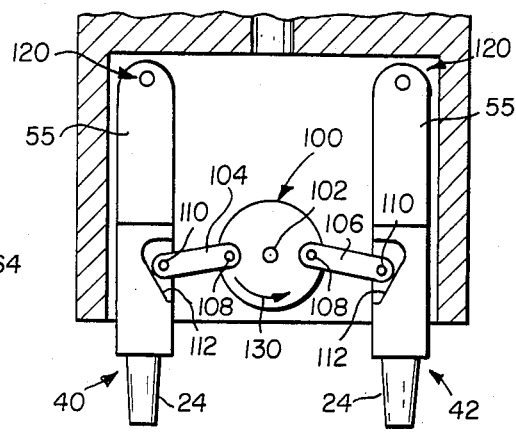
FIG. 5 is an enlarged fragmentary view in section, of a different portion of the elevational view of FIG. 1, with the piston rods and control knob removed for clarity.
Figure 6:
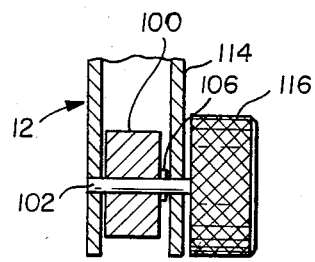
FIG. 6 is a fragmentary section view taken generally along the line VI—VI of FIG. 1, but with a piston chamber removed for clarity.

To allow chambers 40 and 42 to pivot under the action of knob 116, pin 102, disc 100 and links 104 and 106, flanges 55 of the chambers are pivotally mounted on frame 12, FIGS. 3 and 5, at end 120 thereof.

Operation

Figure 7:
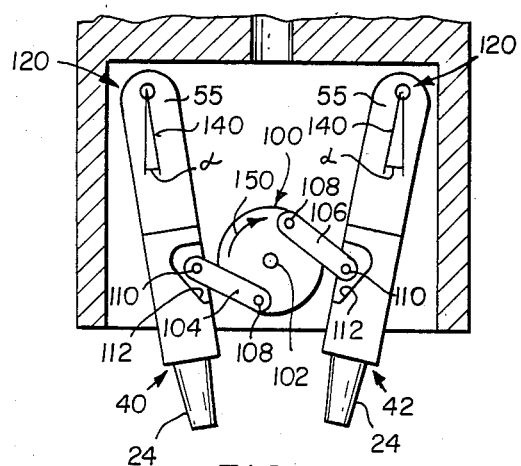
FIG. 7 is the same view as FIG. 5, but with the parts moved to a different position adapted for mixing.

The moving action of knob 116 and its interconnections to chambers 40 and 42 is apparent from FIGS. 5 and 7. When knob 116, not shown in these views, is rotated counterclockwise, disc 100 rotates counterclockwise (arrow 130). Links 104 and 106 in turn pivot also, FIG. 7, so as to come closer together. This in turn pulls chambers 40 and 42 closer together about their pivot points at ends 120. More specifically, each axis 140 of chambers 40 and 42, FIG. 7, is rotated through an equal but opposite angle alpha measured from the generally parallel positions the chambers previously occupied as shown in FIG. 5. To move the chambers back to the position of FIG. 5, rotation is reversed, as indicated by the clockwise arrow 150, FIG. 7.

The preferred, overall use of the pipette, apparent from the preceding discussion, is as follows. With the piston chambers 40 and 42 in their spaced-apart position as shown in FIG. 1, empty disposable containers $C_1$ and $C_2$ are fitted onto nipples 24 so as to be generally parallel to each other with platforms 28 aligned in generally a common plane. Pipette 10 is then positioned above two relatively larger containers of liquids, not shown, spaced apart on center the same distance that containers $C_1$ and $C_2$ are spaced apart. Most preferably, one of the liquids is a patient's sample of body liquid, such as serum, and the other is a diluent, such as a water-based solution or mixture of labeled antigens or antibodies. Button 82 is fully depressed until it contacts a stop such as the top surface of end 16. While button 82 is held down, containers $C_1$ and $C_2$ are inserted into their respective liquids. Button 82 is then released to aspirate the liquids into their respective containers $C_1$ and $C_2$.

Figure 8A:
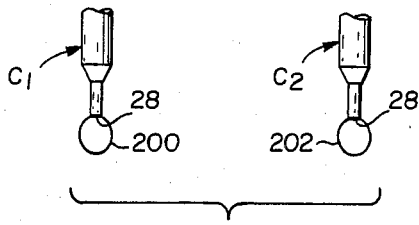
FIGS. 8A through 8D are schematic views of the disposable containers and their pendent drops, illustrating the operating sequence of the device.

Pipette 10 is then removed, preferably to a station containing a test element. As shown in FIG. 8A, button 82 is depressed an amount sufficient to form drops 200 and 202, pendent from platforms 28. If the pipette is a "single-shot" pipette, the volume of such drops is approximately the same as was aspirated, for example, between about 5 and about 10 $\mu$l.

Figure 8B:
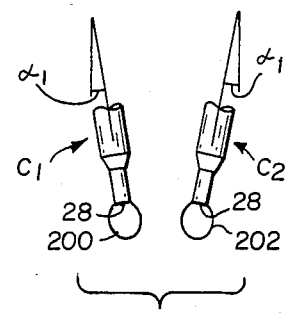
Figure 8C:
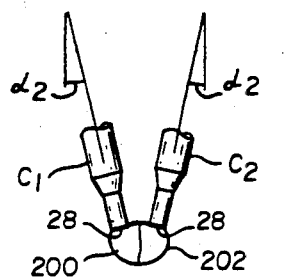

While button 82 is still depressed to keep the drops pendent from their platforms, knob 116 is rotated counterclockwise, FIG. 1, to cause chambers 40 and 42, and their containers $C_1$ and $C_2$, to pivot towards each other, FIG. 8B. The pivot angle alpha for both containers is $\alpha_1$ at this time. Slot 62 allows end 56 of rods 50 and 52 to move towards each other, FIG. 4. Knob 116 is rotated further, until angle alpha equals $\alpha_2$ and platforms 28 are so close that drops 200 and 202 coalesce, FIG. 8C. Mixing immediately commences, at a rate that is generally proportional to the difference between the surface tensions of the liquids of the two drops, and inversely proportional to their viscosities. If desired, spring-biased detents, not shown, are useful to temporarily hold the piston chambers and their containers $C_1$ and $C_2$ in either of their two extreme positions that produce angle alpha equal to zero (FIG. 8A) or to $\alpha_2$ (FIG. 8C). Such detents, if used, are mounted on the undersurface of knob 116 so as to ride over surface 114 of frame 12, FIG. 6, until they seat in recesses, also not shown, that are aligned with such values of angle alpha.

Figure 8D:
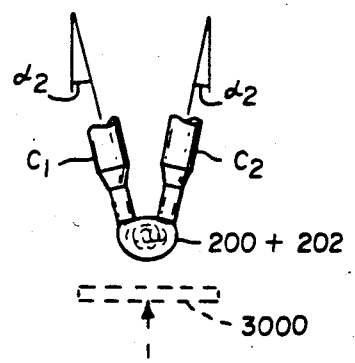

After the desired amount of mixing has occurred, the coalesced drop 200–202, FIG. 8D, is touched off onto a suitable test element 3000.

Thereafter, knob 116, FIG. 1, is rotated clockwise to return the containers $C_1$ and $C_2$ to their FIG. 1, spaced-apart position (wherein angle alpha equals zero). Containers $C_1$ and $C_2$ are then preferably removed for discarding.

It will be readily appreciated that an advantage in having the containers moved from their first position, shown in FIG. 8A, to the position shown in FIG. 8C, and back again is that it is the first position in which the disposable containers $C_1$ and $C_2$ are readily mounted and demounted. Furthermore, the first position is preferred, and indeed required compared to the position of FIG. 8C, for aspiration. Still further, it is preferred, though not essential, that the pendent drops be formed while the containers are in the positions shown in FIGS. 8A or 8B, rather than 8C. The reason is that, such spaced-apart positions allow each drop to form independently, a step that is visually or optically detectable.

Figure 8E:
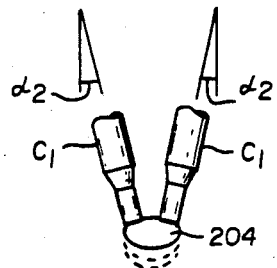
FIG. 8E is a schematic view similar to FIGS. 8A-8D, but illustrating an alternative use of the device.

The alternative use suggested above is demonstrated in FIG. 8E, wherein ejection of the liquids to form pendent drops does not occur until the containers are moved to their proximate positions, wherein $\alpha = \alpha_2$. When button 82 is depressed, the liquids almost immediately form a single pendent drop 204 that increases in diameter, as shown in dashed lines, until the drop is fully formed.

Figure 9:
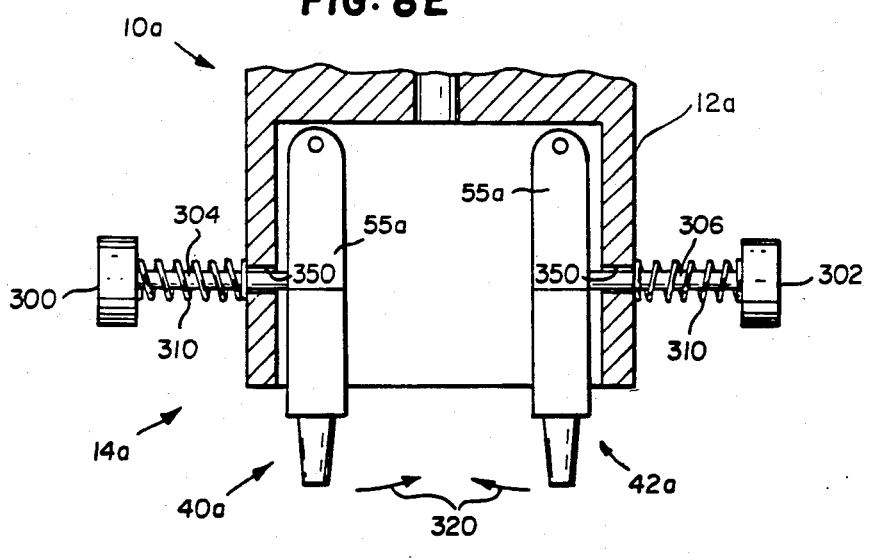
FIG. 9 is an elevational view similar to that of FIG. 5, illustrating an alternate embodiment.

Alternatively, unlike the previously described embodiments, it is not necessary that the moving means be connected to the piston chambers and the containers so as to move both containers simultaneously, through equal but opposite angles of rotation from their spaced-apart, parallel position. FIG. 9 illustrates an alternate embodiment wherein each container is independently movable from its first, parallel position, without necessarily equalling the amount or the time of movement of the other container. Parts similar to those previously described bear the same reference numeral, to which the distinguishing suffix "a" has been added. Thus, pipette 10a features a dispensing end 14a, and an actuating end (not shown), provided with piston chambers 40a and 42a, and piston rods and plunger (not shown) constructed as described before. However, the moving means comprises buttons 300 and 302, each for its own piston chamber, mounted on a plunger 304 and 306, respectively, that connects with flange 55a of the piston chamber. Compression return springs 310 surround plungers 304 and 306, mounted between buttons 300 and 302 and the frame 12a of the pipette. When a button 300 or 302 is pressed against the action of its spring, each container independently pivots inwardly, arrows 320, towards the other container. Preferably, but not necessarily, the pivot amounts of the two containers are selected to be generally equal by applying generally equal pressure to buttons 300 and 302. Holes 350 in frame 12a for the passage of plungers 304 and 306 are made wide enough to accommodate the slight vertical displacement due to the pivotal motion.

In yet another alternative embodiment, a multi-drop pipette can incorporate the invention so that a multiple of the volume of the pendent drop is aspirated into containers $C_1$ and $C_2$ for sequential, multiple drop formation. In such a case, a conventional ratchet mechanism, not shown, is added to insure that liquid increments of from about 5 to about 10 $\mu$l are metered in successive drops.

The invention has been described in detail with particular reference to preferred embodiments thereof, but it will be understood that variations and modifications can be effected within the spirit and scope of the invention.

What is claimed is:

1. A method of mixing two low relative viscosity liquids, the method comprising the steps of
   (a) forming a drop of each liquid so as to be pendent from separate respective platforms, and
   (b) during or after said step (a), moving said platforms from a first spaced-apart position to a second position in which drops pendent from said platforms coalesce while still pendent from said platforms, and intermix.

2. A method as defined in claim 1, wherein said forming step comprises the step of forcing each liquid to flow out of a container through an aperture that is generally centered on its respective platform, in an amount that will cause said drop to be pendent from its respective platform.

3. A method of mixing two low relative viscosity liquids outside of a container, the method comprising the steps of forming a drop of each liquid so as to be pendent from separate respective platforms, and thereafter moving said platforms from a first spaced-apart position to a second position in which the drops coalesce while still pendent from said platforms, and intermix.

4. A method as defined in claim 3, wherein said forming step comprises the step of forcing each liquid to flow out of a container through an aperture that is generally centered on its respective platform, in an amount that will cause said drop to be pendent from its respective platform.

5. A method of mixing two low relative viscosity liquids, the method comprising the steps of
  (a) aspirating said liquids into separate respective containers,
  (b) forming a drop of each liquid so as to be pendent from separate respective platforms on said respective containers, and
  (c) before, during or after said step (b), moving said platforms from a first spaced-apart position to a second position in which drops pendent from said platforms coalesce while still pendent from said platforms, and intermix.

6. A method as defined in claim 5, wherein said forming step comprises the step of forcing each liquid to flow out of its respective container through an aperture that is generally centered on its respective platform, in an amount that will cause said drop to be pendent from its respective platform.

* * * * *